United States Patent [19]
Busson et al.

[11] Patent Number: 5,554,347
[45] Date of Patent: Sep. 10, 1996

[54] APPARATUS FOR CARRYING OUT CHEMICAL REACTIONS REQUIRING ADDITION OF HEAT AT LEAST DURING START UP

[75] Inventors: Christian Busson, Charbonniere; Henri Delhomme, Sainte Foy Les Lyon; Laure Gollion, Paris; Jean Pierre Cassagne, Fontenay Sous Bois, all of France

[73] Assignees: Institut Francais Du Petrole, Rueil Malmaison; Gaz De France, Paris, both of France

[21] Appl. No.: 382,599

[22] Filed: Feb. 2, 1995

[30] Foreign Application Priority Data

Feb. 2, 1994 [FR] France ................... 94 01243

[51] Int. Cl.⁶ .................. F28D 21/00; B01J 19/24
[52] U.S. Cl. .............. 422/204; 422/198; 422/200; 422/201; 422/207; 165/142; 431/116; 431/353
[58] Field of Search ................... 422/198, 200, 422/201–205, 207; 585/913; 431/9, 115–116, 353; 126/91 A, 91 R; 165/142

[56] References Cited

U.S. PATENT DOCUMENTS

| 2,163,599 | 6/1939 | Houdry | 422/200 |
|---|---|---|---|
| 4,298,333 | 11/1981 | Wunning | 431/11 |
| 4,479,534 | 10/1984 | Rhodes | 165/142 |
| 4,694,896 | 9/1987 | Navratil | 165/142 |
| 4,850,334 | 7/1989 | Cassagne et al. | 431/353 |
| 4,894,006 | 1/1990 | Cassagne et al. | 431/116 |
| 5,160,501 | 11/1992 | Alagy et al. | 585/500 |
| 5,270,016 | 12/1993 | Alagy et al. | 422/199 |

FOREIGN PATENT DOCUMENTS

| 323287 | 7/1989 | European Pat. Off. . |
|---|---|---|
| 0539270 | 4/1993 | European Pat. Off. . |
| 2403518 | 4/1979 | France . |

OTHER PUBLICATIONS

"Cerajet: gas fired radiant tube for indirect heating of high–temperature industrial furnaces", Scrive et al., *Rev. Gén. Therm. Fr.*, No. 346, Oct. 1990, pp. 531–538.

*Primary Examiner*—Robert Warden
*Assistant Examiner*—Hien Tran
*Attorney, Agent, or Firm*—Millen, White, Zelano, & Branigan, P.C.

[57] ABSTRACT

The invention relates to an apparatus comprising a reactor, elongated along one axis, preferably of square or rectangular cross section. The reactor has, at one extremity, at least one supply line for at least one reactant and at least one evacuation outlet at the other extremity for removal of produced effluents. In a first zone (near the first extremity of the reactor), a plurality of heat exchangers, substantially parallel to each other, are disposed in substantially parallel layers perpendicular to the reactor axis, thereby defining spaces or passages for circulation of reactant(s) and/or effluents between the heat exchangers and/or layers formed by the heat exchanger. The heat exchangers are adapted to exchange heat in the passages through successive transverse sections, which are independent and substantially perpendicular to the reactor axis. At least some of the heat exchangers comprise a tubular element formed by at least one shell, supplied with a heat exchange gas or gas mixture, and at least one evacuation element for evacuating the circulating gas or gas mixture which has undergone heat exchange with the reactant(s) and/or effluents.

26 Claims, 3 Drawing Sheets

FIG.1C

APPARATUS FOR CARRYING OUT CHEMICAL REACTIONS REQUIRING ADDITION OF HEAT AT LEAST DURING START UP

SUMMARY OF THE INVENTION

The present invention concerns an apparatus for carrying out chemical reactions which require the addition of heat at least during start up. This apparatus generally comprises a series of elements which, at least in a first zone, supply heat necessary for the reaction to start. This apparatus can be used for reactions which are exothermic in total, but require the addition of heat during start up, such as catalytic hydrogenation reactions. This apparatus is particularly applicable for use with any endothermic reaction but more particularly for use in steam cracking, pyrolysis, catalytic hydrogenation and catalytic steam reforming of hydrocarbons or hydrocarbon cuts in which the reaction temperature is often greater than about 350° C. and where one of the problems which must be overcome is limiting secondary reactions which lead to the formation of tar and/or coke.

Many documents describe processes and apparatus for carrying out these processes. Particular examples are U.S. Pat. No. 4,780,196 and U.S. Pat. No. 4,973,777 from the Institut Francais du Pétrole, which respectively describe a pyrolysis process carried out in the presence of steam, termed steam cracking, and a process for the thermal conversion of methane carried out in a multichannel ceramic reactor. The steam cracking process produces ethylene and propylene in high yields and the thermal coupling process, which dehydrogenates methane, produces acetylene, ethylene and aromatic compounds in high yields. However, the reactor design is critical, the ceramics used to construct it are relatively expensive and it is difficult to maintain a constant temperature throughout the length of the reaction zone, which has deleterious effects on the process. Further, controlling the reaction throughout the reaction zone in this type of reactor is very difficult in the case of steam cracking and a heating fluid must be used as a heating means which circulates in channels. With electrical heating for methane conversion, the lifetime of the resistors is shortened by higher temperatures in the reaction zone. This reactor design is also critical and controlling the transverse heating sections requires complex systems such as control led transformers and thyristor modulators.

Thermodynamic and kinetic studies of these reactions, in particular hydrocarbon pyrolysis reactions and those concerning thermal conversion of methane, have shown that in order to increase the selectivity of the reaction towards production of the desired products (olefins or mixtures of olefins, acetylenes and aromatics), the following parameters must be controlled:

the temperature of the feed must be rapidly raised to the optimum temperature for pyrolysis of a given feed, and this temperature must be held as constant as possible in the reaction zone;

the residence time of the feed in the reaction zone must be reduced:

the partial pressure of the hydrocarbon feed must be reduced.

It is also particularly important to minimize the contact time between the reaction products and the reactor walls.

These requirements rapidly led to a general scheme for the process consisting of:

a) preheating the feed (which may be diluted with steam, or hydrogen, nitrogen or another gas depending on the reaction to be carried out);

b) heating the feed, feed-steam mixture or feed-diluting gas mixture to a high temperature in tubular furnaces to limit the residence time of the hydrocarbons during this phase of pyrolysis.

The development of pyrolysis furnaces, in particular for steam cracking, has mainly been directed towards obtaining shorter residence times and reducing the pressure drop. This has led designers to reduce the length of the tube reactors and increase the thermal flux density.

The latter factor can be increased by raising the temperature of the tube reactor shell and/or reducing the tube diameter (which means that the ratio s/v can be increased, where s is the exchange surface and v is the reaction volume).

A number of pyrolysis furnace designs have also been developed, all tending to increase the thermal flux density at the beginning of the pyrolysis tube and subsequently reduce it, either by using tube reactors with increasing diameters, or by using at least two pyrolysis tubes and only one after a certain length along the reaction zone (see, for example, the article by F WALL et al, published in Chemical Engineering Progress, December 1983, pp 50 to 55). Noncylindrical tube furnaces have also been described, which tend to increase the s/v ratio; thus U.S. Pat. No. 3,572,999 describes the use of oval section tubes and U.S. Pat. No. 3,964,873 describes tubes with a dumbbell shaped cross section.

Pyrolysis reactor technology, in particular steam cracking technology, has thus evolved from the use of horizontal tubes about 100 meters (m) in length and with internal diameters of the order of 90 to 140 millimeters (mm) to the conventional technology of vertically suspended tubes of about 40 m in length and a diameter of the order of 60 mm operating with residence times of the order of 0.3 to 0.4 seconds (s), and finally to the so-called millisecond process developed by PULLMAN-KELLOG (U.S. Pat. No. 3,671,198) which uses vertical rectilinear tubes of about 10 m in length with an internal diameter of 25 to 35 mm. These tubes are heated to temperatures on the order of 1100° C. (which is frequently close to the operating limits of the metal). The residence time of the feed in this type of furnace is on the order of 0.07 s; the pressure drop observed is of the order of 0.9 to 1.8 bar (1 bar equals 0.1 megapascal), and the ratio of the exchange surface s to the reaction volume v is on the order of 120 $m^{-1}$.

One of the major problems in carrying out pyrolysis, in particular steam cracking of hydrocarbons, is the formation of coke on the reactor walls. This is largely due to secondary reactions such as the formation of condensed polycyclic aromatic hydrocarbons. These reactions are greatly affected by the temperature: above 900° C., an increase of 50° C. in the temperature of the reactor walls doubles the rate of deposition of coke on these walls. Regardless of the process, this coking phenomenon means that the unit must be stopped for decoking. The smaller the space between the walls, the worse the effect.

With a view to overcoming the problems described above, European patent EP-B-0 323 287 and U.S. Pat. No. 5,160, 501 from the Institut Francais du Pétrole describe processes for the thermal conversion of methane to higher molecular weight hydrocarbons, comprising electrical heating means with heat transfer to the gaseous mixture containing the methane to be converted, through the sealed or non sealed walls of ceramic sleeves which isolate the heating means from the gaseous mixture containing the methane. In this process, the heating zone is heated by electrical energy provided by resistors and the heat released in these resistors by the Joule effect is transmitted, mainly by radiation, to the ceramic sleeves positioned noncontiguously around the resistors. The gaseous feeds which circulate substantially perpendicularly to the axes of the heated sleeves, are mainly heated by convection. One of the main drawbacks of these embodiments lies in the difficulty of producing a high temperature at the sleeve exterior without having to maintain the resistors at a temperature close to the maximum that the material from which they are made can support, implying a relatively short lifetime for these resistors and frequent stopping of the industrial unit in order to change them. It is also very important to avoid, as far as possible, the appearance of hot spots on the exchange surfaces. Further, in the apparatus described in these patents, the seals are made dynamically when hot, by injecting a gas into the resistor sleeves, which constitutes a major problem when a breakdown occurs in just one sleeve, necessitating shutting down the entire installation. In addition, while the sleeves can form heating elements when the resistors are supplied with electric current, or passive elements when not supplied with electric current, they can never be used as indirect cooling elements for the products circulating in the furnace. Finally, the temperature over the length of the tube shell is not very homogeneous.

U.S. Pat. No. 2,163,599 describes a heat exchanger comprising concentric double or triple tubes containing, in a first annular shell, a liquid heat exchange fluid such as water, brine or oil which circulates. This shell is surrounded by a further sealed annular shell in which mercury, lead, various fusible alloys, diphenyl or molten salts are stored to act as a buffer. External ties are fixed to the last shell to facilitate heat exchange with the outer wall of the tube. This type of tube exchanger cannot be used at reaction temperatures which can reach 1500° C. without a system for rapidly adjusting the temperature level in the reactor.

The state of the art is illustrated in French patent FR-A-2 403 518, EP-A-0 539 9-70 and U.S. Pat. No. 5,160,501, also the article in "Revue Générale de Thermique", vol 29, no 346, Oct 90, Paris, France, pp 531 to 538. One of the objects of the invention is to overcome the problems described above. These objectives, which respond to the problems raised by the prior art, are essentially as follows:

to be more homogeneous in temperature throughout the tube enveloping the heat exchange means, which should produce better chemical yields;

to improve the heat exchange between the reactant(s), and the hot surfaces in contact with the mixture:

to increase the reliability of the apparatus and its ease of construction and dismantling for decoking and maintenance. In particular, the apparatus must be capable of continuing to operate even in the event of a breakdown in one of more heat exchange means;

to better control the reaction temperature profiles, which thus increases the yields of the desired products, such as ethylene and propylene in the case of steam cracking of hydrocarbons, compared with existing processes;

to provide an apparatus which is both versatile and flexible in production and which uses control modes, for example by starting/stopping at variable speeds or at high frequencies while retaining the highest possible productivity of required products:

to provide an apparatus in which the seals are made when cold at the reactor walls. This means that additional separation of the products downstream of the reactor can be dispensed with when the sealing gas is different to the products leaving the reactor and results in less gaseous effluent which has to be treated;

to provide an apparatus in which the geometry of the reaction zone can be varied and thus allow a reactor with a fixed geometry to be operated with very different feeds;

to provide an apparatus which can operate either with a direct quenching zone, which may be coupled with an indirect quenching zone, or with only an indirect quenching zone;

to provide an apparatus in which each heat exchange means can function as a heating element, as a cooling element or as a passive element.

The present invention provides an apparatus for carrying out various processes, in particular those described above, which represents a considerable improvement over the prior art, such as easier, more flexible and better controlled operation. Its versatility is linked to the use of heat exchange elements which can be completely independent of each other and which can be used as heating elements, cooling elements or passive elements.

More particularly, the invention concerns an apparatus for carrying out reactions requiring addition of heat at least during start up, more particularly for carrying out endothermic reactions. For simplicity, the remainder of the description will refer to using the apparatus of the invention for carrying out endothermic reactions, more particularly for performing methane pyrolysis or pyrolysis of hydrocarbons containing at least 2 carbon atoms per molecule. The description should not, however, be considered to limit the apparatus of the invention to this use.

The apparatus of the present invention comprises a reactor (1) which is elongate along one axis, preferably of square or rectangular cross section, comprising at least one supply means for at least one reactant at one extremity, and at least one evacuation means at the other extremity for the effluents produced. The reactor comprises, in a first zone (near the first extremity), a plurality of heat exchange means (3) which are substantially parallel to each other. The heat exchange means (3) are disposed in substantially parallel layers perpendicular to the reactor axis to define spaces or passages between the means and/or layers formed by the means for the circulation of reactant(s) and/or effluents. The heat exchange means (3) are adapted to exchange heat in the passages through successive transverse sections, which are independent and substantially perpendicular to the reactor axis. The apparatus is characterized in that each of the heat exchange means (3) comprises a tube formed by at least one shell, connected to a means for supplying a heat exchange gas or gas mixture adapted to exchange heat with the reactant(s) and/or effluents circulating outside the heat exchange means (3). The reactor further comprises at least one evacuation means for evacuating from the reactor the gas or gas mixture that has exchanged heat with the reactant(s) and/or effluents.

In a particular embodiment, all or a part of the heat exchange means supplied with a heat exchange gas or gas mixture communicate with gas burners connected to means for supplying a fuel gas and an oxidizer gas, and means for controlling the burners and adjusting the quantity of gas supplied to the burners which are interposed between the supply means and the burners (see 51 in FIG. 2), so that the heat exchange means are supplied either with the combustion product from the burners or exclusively with oxidized gas.

Within the context of the present invention, the tube comprises at least one shell which may have any cross sectional shape, for example, polygonal, oval or substantially circular. When a tube with a shell with a polygonal cross section is used, the cross section is advantageously triangular, square, rectangular, pentagonal, hexagonal, heptagonal or octagonal. More frequently, this cross section is square, rectangular, oval or substantially circular. Most frequently, the cross section is substantially circular. It is not necessary for either the shape or surface of the cross section to be constant over the entire length of the tube. However the cross section is most often constant in shape and preferably also in surface.

The shape of the tubes is not critical and tubes comprising a shell which is elongate along one axis, hairpin shaped tubes or U shaped tubes, or W shaped tubes can be used. It is generally prefered to use tubes comprising a shell which is elongate along one axis. Different shaped tubes can be used along the length of the reactor. U or W shaped tubes can be used, for example, at the start of the reactor, close to the reactant(s) input, followed by tubes with a shell which is elongate along one axis. U or W shaped tubes can also be used close to the reactor extremity which is opposite to end at which the reactants enter the reactor.

In a preferred embodiment of the invention, at least some of the heat exchange means (3) are formed by a blind tube formed by an outer shell which is closed at one extremity and an inner shell which is substantially coaxial with said outer shell, open at its two extremities and supplied with the heat exchange gas or gas mixture at one of its extremities. The heat exchange gas or gas mixture is evacuated at the other extremity into the free space ( often termed the annular space, although this does not limit the shape of this space to a circular form) between the two shells.

Figure 2:
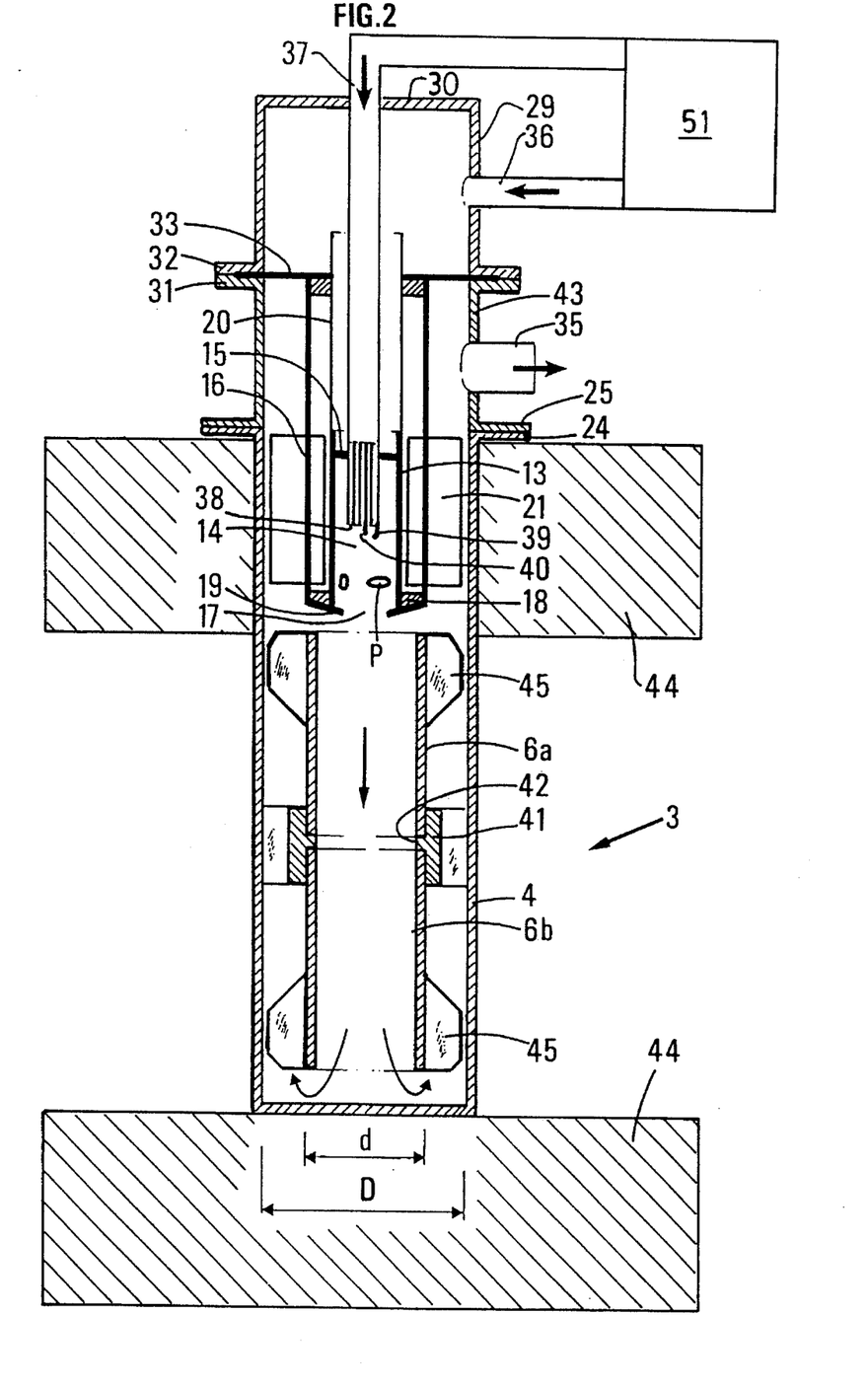
FIG. 2 shows a longitudinal section along the axis of a heat exchange means, detailing a heating means comprising a self regulating jet burner.

In order that the temperature along the length of the outside of the outer shell of the blind tube is as homogeneous as possible, and the circulation of the gases in the annular space between the two shells is good, it is usually preferred that the ratio of the internal area ($s_e$) of the cross section of tube forming the outer shell of the blind tube to the external area ($s_i$) of the cross section (the areas being calculated from diameters D and d of the circular cross section tubes using the embodiment shown in FIG. 2) of the tube forming the inner shell of the blind tube is about 1.4:1 to about 25:1, preferably about 2:1 to about 9:1. Under these conditions of area ratios, homogeneity of temperature is ensured such that the maximum variation along the outer tube is at most 30° C.

In a preferred embodiment, the apparatus of the present invention comprises a reactor containing, in a second zone (8) (near the opposite extremity) which is contiguous with the first zone, means (9) for cooling the effluent connected to at least one means for supplying cooling fluid. It is usually preferable that the reactor includes means for controlling and adjusting heat exchange connected to the heat exchange means (3).

The versatility is linked to the use of heat exchange elements which can be completely independent from each other and which can produce a reaction zone of variable length without being limited at outset by the reactor geometry, as will be shown in the examples. The heat exchange elements can be heating elements, cooling elements or passive elements and thus the lengths of the different zones and the temperatures in these zones can easily be varied.

The heat exchange means are usually substantially perpendicular to the product(s) flow in the reactor and, in transverse projection, form an array with a triangular, square or rectangular spacing pattern. These means can be assembled in successive transverse sections which are substantially perpendicular to the direction (axis) of the reaction zone, are independent of each other and supplied with heating gas so as to determine at least two portions in the first zone, the heating zone. The first portion heats the feed to a temperature of at least about 1500° C. and the second portion, which follows the first portion, holds the feed at a temperature substantially equal to the maximum temperature to which it is raised in the first portion. In the second zone, which follows the first zone, the effluents from the heating zone are cooled and the products formed are recovered at the end of the reaction zone. It is thus possible to provide one or more heat exchange means in the second zone of the reactor which are used as elements for cooling the effluents leaving the second portion of the heating zone by indirect heat exchange and either to recover the products formed at the end of the cooling or quenching zone, or to provide, after this indirect quenching zone, a direct quenching zone to recover the products at the output of this direct quenching zone.

Thus in one embodiment of the apparatus of the invention, the reactor is constituted (near the first extremity) by a first zone in which at least some and preferably the majority of the heat exchange means of the first zone form heating means for the reactant(s) introduced into the reactor, and a second zone in which at least some and preferably the majority of the heat exchange means in this second zone form cooling or indirect quenching means for the products from the first zone.

In these embodiments, the heat exchange means in the first zone can be supplied with a combustion gas at high temperature, preferably from a burner supplied with fuel and oxidizer such as air. Also, the heat exchange means of the second zone are each supplied with at least one gas at a lower temperature than that of the combustion gas supplying the first zone, preferably gases from a burner supplied solely with an oxidizer such as air.

In the case of steam hydrocarbon cracking, which is carried out at a temperature on the order of 800° C. to 1300° C., and in the case of thermal dehydrogenating coupling of methane which is carried out at a temperature of the order of 1100° C. to 1500° C., both of which are strongly endothermic reactions, it is vital that a very high thermal flux density is obtained. The maximum amount of heat must be brought into the zone where the endothermic cracking and dehydrogenation reactions occur. In addition, because of the reactivity of the products formed, such as acetylene, ethylene and/or propylene, the contact time must be controlled, relatively short and followed by rapid quenching to obtain a "square" temperature profile and avoid too much coke formation.

Heat exchange is one of the key elements in this type of highly endothermic reaction where very large quantities of energy must be transferred from the heat exchange means used for heating to the gas mixture containing at least one hydrocarbon, termed the process gas. During our preliminary study on heat exchange in a pyrolysis furnace constructed in accordance with the model used in the present invention, it was observed that there was generally only a little radiative exchange between the outer shell of the heat exchange means and the process gas. This latter is normally mainly constituted by a mixture of hydrocarbons and diluting gases, which absorbs little of the radiation emitted by the shell. Heat transfer between the process gas and the shell is thus principally effected by convection in the case envisaged by the present invention. In this case, the quality of heat exchange is directly linked to the available exchange surface area, the surface/volume ratio and to good homogeneity of temperature in the heat exchange means.

Thus, if the exchange surface is relatively low, in order to obtain a temperature in a given process gas which corresponds to a selected conversion rate, it will be necessary to increase the shell temperature of the heat exchange means, by a greater amount if the surface is smaller, increasing the risk of coke formation.

The walls play a large role in heat exchange, since they are capable of absorbing the radiation emitted by the shells of the heat exchange means and thus the temperatures of these shells and the walls tend to equilibrate. It is thus possible to increase the exchange surface considerably and almost double it by designing the apparatus in a particular way. While the heat exchange means can be arranged in staggered fashion, it is preferable to increase the exchange surface by aligning the heat exchange means. Thus n rows of m heat exchange means can be disposed in the longitudinal direction (for a total number of heat exchange means of n x m), to form at least one longitudinal zone and most often at least two longitudinal zones each comprising one and often a plurality of layers of heat exchange means, each longitudinal zone being separated from the next zone by a wall of refractory material. The heat exchange surface can thus be increased by optimizing the surface area such as by adding fins to the outer shells of the heat exchange means participating in heat transfer.

The temperature of these walls increases due to radiation and tends to be a value very close to that of the outer shells of the heat exchange means. These walls thus also participate in convection heating of the process gas. Thus in this embodiment, since the exchange surface has been considerably increased, the process gas can be brought to the same temperature with a relatively lower temperature of the outer shells of the heat exchange means and walls, therefore reducing coke formation.

In one particular embodiment, each longitudinal zone comprises a single row of heat exchange means.

In these two embodiments, convectional exchange between the process gas and the walls is greatly increased and can be improved still further by forcing the process gas to reach high speeds and create turbulence zones. The increase in the speed of the process gas can, for example, be obtained by using walls whose shape favors this increase in speed and the appearance of turbulence zones. Some non limiting examples of particular forms of walls are shown in FIGS. 1B and 1C.

The walls are generally formed of refractory material. Any refractory material can be used for the walls; non limiting examples are zirconia, silicon carbide, mullire and some refractory concretes.

Since it is not at all necessary to seal the walls, since the gas composition is practically identical on each side of the walls, this embodiment only minimally increases the cost of the apparatus. In fact, it is not necessary to have especially thick walls, nor use an especially complex construction, and the overall dimensions of the reactor are only slightly increased since the bulk of the reactor width is due to the width of the outer shells of the heat exchange means. By way of example, these shells can have a width on the order of 165 mm for a wall thickness on the order of 50 mm, meaning that the overall width of the reactor is increased by only a percentage on the order of 30%.

An additional advantage of this embodiment which includes walls is that the construction of the reactor is more simple, the vertical walls both improving convectional heat transfer and supporting the reactor roof.

In addition, it is preferable that each wall includes at least one means for equilibrating the pressures in the longitudinal zones situated either side of the wall. An example of a simple but effective means for equilibrating the pressures is to create zones comprising one or more perforations or porous zones.

In a further embodiment, the reaction zone can also include a series of elements termed passive heat transfer elements whose main functions are to increase the exchange surface, limit the residence time and change the velocity of the reactants. These passive heat transfer elements can also be used in combination with the refractory material walls, in particular when there are several layers of heat exchange means between two walls. These walls and the passive heat transfer elements, which in the case of carrying out endothermic reactions are, in at least a first portion of the reaction zone, heating elements, participate in heat exchange by absorbing then re-emitting a portion of the radiation emitted by the heat exchange means.

In a still further embodiment, the heating and/or reaction zone contains lining elements whose constituent materials are preferably selected from the group formed by refractory materials. These lining elements can be constituted by a refractory concrete, a monolithic ceramic or a ceramic fiber. They are thus either divided elements, or solid elements which can thus be considered to act as passive elements in the reaction zone, as described above. Divided and solid elements can be present together. These lining elements are often used to limit the residence time and adjust the velocity of the process gas (reactant and/or products formed) in the reaction zone. These elements, when they are solid elements, can also serve as supports for the outer walls which are at least partially formed from refractory materials. They can also have dimensions such that they are only connected to one outer wall and thus act as a chicane to increase the available surface for exchange between the process gas and the heat exchange means.

In one particular embodiment, in which one of the advantages is still greater flexibility of the apparatus of the invention, the reactor comprises tubular heat exchange means comprising a shell which is not supplied with gas or a gas mixture. The means thus forms passive heat transfer elements.

In another embodiment, this tube is a blind tube, comprising an outer shell which is closed at one of its extremities, and an inner shell, which is substantially coaxial with the outer shell, open at both extremities and not supplied with gas or a gas mixture. The means thus forming passive heat transfer elements.

The heat exchange means which supply heat to the heating zone are independently supplied, either in isolation, or in transverse sections, to define heating sections along the heating zone and thus to adjust the quantity of energy supplied along the whole length of this zone.

The heating zone is normally composed of 2 to 20 heating sections, preferably 5 to 12 sections. In the first portion of this zone, the gaseous mixture includes at least one hydrocarbon which has been heated to about 400° C. to 1000° C., and normally heated to a temperature of at least 1500° C., advantageously between 800° C. and 1300° C. (the start of the heating zone is located at the position where the reactant(s) are introduced).

Modulation of these heating sections is carried out conventionally: the heat exchange means corresponding to the sections defined above ere generally supplied under fuel add oxidizer gas flow conditions which can produce the desired temperature at the exterior of the outer shell of each heat exchange means.

In order to regulate the apparatus, each heating section can be provided with temperature sensors: these sensors are located in the spaces in which the feed circulates and data is transmitted to the control unit which controls the fuel and oxidizer gas flows.

The first portion of the heating zone is generally at least 5% of the total length of the heating zone, advantageously at least 20%, for example 20% to 90%.

The energy supplied to this first portion of the heating zone is such that a steep temperature gradient is generated which produces a relatively high average temperature of the feed in the heating zone. This temperature gradient is generally about 0.5 to about 25° C./cm. In the case of hydrocarbon pyrolysis, such as ethane pyrolysis, this favors light olefin selectivity.

In the second portion of the heating zone, the energy supplied to the different heating sections in this zone is adjusted so that the temperature variation throughout the length of this zone is low, in general less than about 50° C. (+ or −25° C. from the set value) and advantageously less than about 20° C. (+ or −10° C. from the set value).

In addition, the use of different transverse heating sections, which are independent of each other, means that in the second portion of the heating zone, the maximum thermal energy can be supplied to the region where the majority of the endothermic reactions occur, and a quasi uniform temperature can be maintained in the remainder of the heating zone.

The heating zone is generally about 50% to about 90% of the total length of the reaction zone.

A very high thermal flux is obtained at high temperature, particularly under the heating conditions described above. This normally implies particular care in selecting the material constituting the outer shells of the blind tubes. Examples of materials which are suitable for these shells are ceramic materials, silicon carbide, boron nitride, silicon nitride and zirconia.

In one particularly advantageous embodiment of the apparatus of the invention, at least some of the heat exchange means (3) comprise a tube supplied with gas or a gas mixture via a burner comprising a shell forming an annular chamber around the burner in which the heat exchange gas or gas mixture circulates then is evacuated from the chamber.

In a preferred embodiment, at least some of the heat exchange means (3) comprise a blind tube supplied with gas or a gas mixture via a burner, comprising a shell forming an annular chamber around the burner in which the heat exchange gas or gas mixture from the annular space between the two blind tubes circulates and is then evacuated from the chamber. In this case, the use of a high velocity jet burner causes efficient recirculation of the gaseous products and results in very good homogeneity of temperature over the entire height of the outer shell tube of the blind tube.

Most frequently, the outer shell of the blind tube and the shell forming the annular chamber around the burner are coaxial and have the same internal diameter. In general, these two shells, i.e., the outer shell of the blind tube and the shell forming the annular chamber around the burner, are formed by a single tube.

The inner shell of the blind tube generally has ribs on its radially outer cylindrical surface to center it in the outer shell of the blind tube.

Advantageously, a heat exchange means is used in which the inner shell of the blind tube includes a plurality of tube sections disposed end-to-end and substantially axially aligned and assembled by assembling means comprising an annular member forming a sleeve which coaxially surrounds the tube sections to connect them at a joint zone and in which the radially inner surface comprises, at the mid point of its length, an annular flange which projects radially inwardly and engages between the two tube sections to be connected. The portions of the inner surface situated on either side of the flange widening gradually towards the extremities of the sleeve. The sleeve usually has ribs for centering the inner shell of the blind tube in the outer shell of the blind tube located on its radially outer surface.

The apparatus of the present invention can advantageously employ a blind tube such as that described in French patent FR-A-2 616 518 (U.S. Pat. No. 4,850,334) and a self regulating jet burner as described in French patent FR-B-2 616 520 (U.S. Pat. No. 5,894,006), all from Gaz de France and incorporated by reference.

BRIEF DESCRIPTION OF THE DRAWING

The invention will be better understood from the following description of several embodiments which are given purely by way of non limiting illustration. In the accompanying drawings, similar means are designated by the same reference numerals and letters. The figures concern a preferred embodiment of a reactor of the invention when using at least one blind tube and at least one jet burner in a process employing endothermic or exothermic reactions.

In FIGS. 1B and 1C, the reactor includes walls which separate one or more layers of heat exchange means.

Figure 1A:
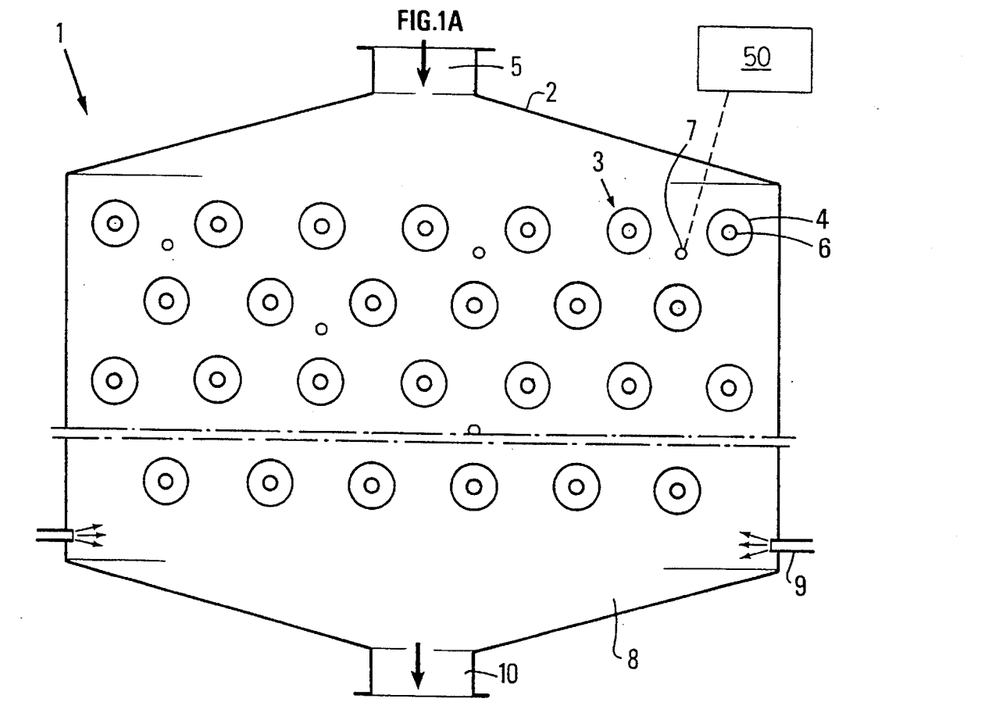
FIGS. 1A, 1B and 1C represent a longitudinal cross section of a reactor through a plane perpendicular to the axes of the shells.
Figure 1B:
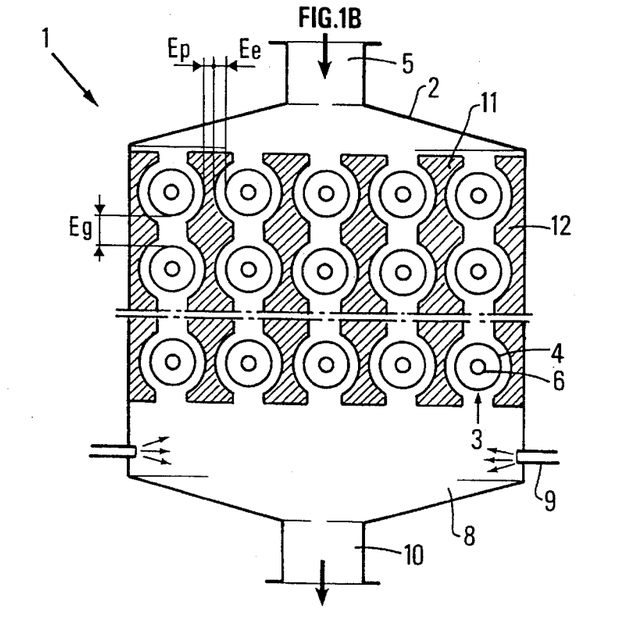
Figure 1C:
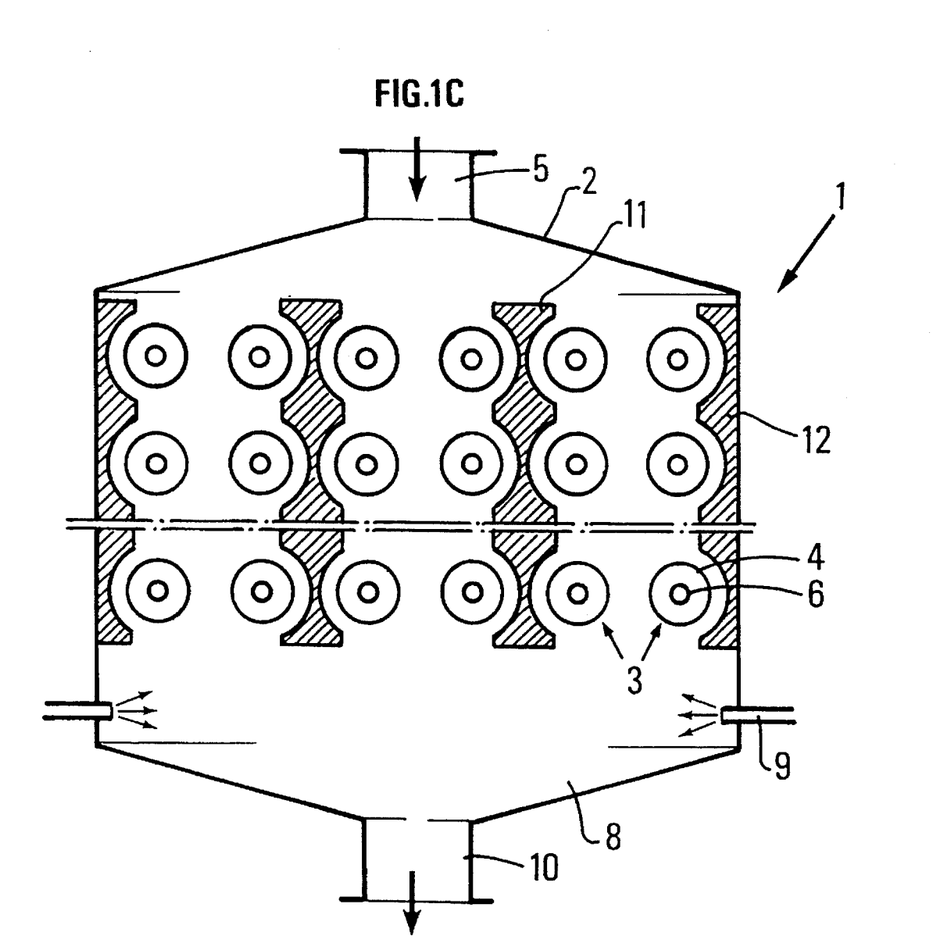

FIG. 1A shows a vertical reactor (1) of elongate form and rectangular cross section comprising a distributor (2) which supplies the reactor with the gaseous reaction mixture via an input orifice (5). The gas mixture contains, for example, 50% by volume of methane and 50% by volume of diluting gas, and is preheated in a conventional preheating zone, not shown in the figure, preferably by convection. The reactor includes a plurality of heat exchange means (3) each comprizing an outer shell (4) and a substantially coaxial inner tube (6), disposed in parallel layers and forming an array with a triangular spacing pattern in one plane (the plane of the figure). These layers define transverse heating or cooling sections which are substantially perpendicular to the reactor axis defined in the direction of flow of the feed.

These heating sections are independently supplied with heat by circulating a gas or a gas mixture introduced into the inner tube (6) and evacuated through the annular space between the inner tube (6) and outer shell (4). Thermocouple thermometer probes (7) are positioned in the spaces in which the feed circulates between the heat exchange means (3) outside the shell (4) and automatically regulate the temperature of each heating section, using a conventional control unit 50.

In the first portion Of the heating zone and for the thermal conversion of methane, the heat exchange means are heated so that the temperature of the feed rapidly passes from the preheating temperature (for example 750° C. or 1000° C.) to about 1200° C. This progressive heating zone generally represents about 25% of the total length of the heating zone. The gas mixture then flows into the second portion of the heating zone where the temperature is normally maintained at a constant value which is substantially equal to that reached at the end of the first heating zone, i.e., about 1200° C. The heating power supplied to the various heating sections which constitute the second portion of the heating zone is adjusted so that the temperature variation is not more than 10° C. from the set value. The second portion of the heating zone is about 75% of the total length of the heating zone.

At the exit to the heating zone, the reaction effluents are cooled in a cooling zone (8). They are brought into contact with a quenching agent such as propane introduced via quenching injectors (9) located at the reactor periphery and connected to an external source of propane, not shown. The gas effluents are cooled to a temperature of about 500° C. and recovered via an output orifice (10) at the end of the reactor.

In another embodiment, the effluents are at least partially cooled on flowing across a zone located after the second portion of the heating zone, in which the heat exchange elements are cooling elements with an inner tube (6) which is supplied with a gas or gas mixture which is relatively cold and is introduced into the inner tube and evacuated from the annular space between the inner tube (6) and the outer shell (4). It is possible, but normally not vital, to follow this cooling by direct quenching in zone (8) as described above.

FIG. 1B shows a vertical reactor (1) of elongate form and rectangular cross section which differs from the reactor shown in FIG. 1A in that it comprises heat exchange means which are disposed in rows of substantially parallel layers which form an array with a square spacing pattern in one plane (the plane of the figure). These rows are separated from each other by walls (11) which are advantageously of ceramic material substantially parallel to the reactor axis. These walls have a shape which is adapted to create turbulence, and include cells near each heat exchange means (3). On the inner surface of its outer walls, the reactor includes a projecting portion (12), advantageously of ceramic material, which has a shape which is adapted to create turbulences, comprising cells close to each heat exchange means (3). The distance $E_g$ separating two neighbouring heat exchange means (3) is not critical but remains fairly low to provide the required residence tame and thermal flux density. It is normally from about 2 mm to about 100 mm. The rows of heat exchange means (3) are separated by a wall, for example of refractory electrosmelted alumina base concrete The distance $E_e$ between the heat exchange means (3) and the walls, or the passage dimension, is normally fairly low to ensure good contact of the gases with the outer surface of the shell (4) of the heat exchange means (3). It is normally from about 1 mm to about 100 mm, preferably from about 2 mm to about 50 mm. At their thinnest parts, the walls have a relatively low thickness $E_p$ which is, however, sufficient to ensure good mechanical behavior of these walls is normally about 2 mm to about 300 mm, preferably from about 5 mm to about 50 mm.

The embodiment shown in FIG. 1C differs from that shown in FIG. 1B only in that a number of layers of heat exchange means (3) are positioned between two walls FIG. 2 shows a longitudinal section along the axis of a heat exchange meads, detailing a heating means comprising a self regulating jet burner.

The burner comprises a thermomechanical ceramic heating tube 13 which delimits a combustion chamber 14 of the burner and is of simple form with a rebate 19 at the outlet extremity for burned gases, to strongly impel the combustion products out of the burner nozzle. On the side opposite to exit 17 defined by rebate 19, combustion chamber 14 is closed by a disk 15 which is preferably transparent. A tubular element 16 coaxially surrounds heating tube 13. At its extremity nearest exit 17 for burned gases, this tubular element is radially narrowed to form an abutment 18 which axially positions heating tube 13 and coaxially surrounds rebate 19. Heating tube 13 bears against this abutment via a radial annular shoulder in rebate 19 and via a sealing joint. Tubular element 16 also coaxially surrounds tube 20 which is positioned so as to extend heating tube 13 at the closing disk 15 side of the combustion chamber. Tube 20 has substantially the same diameter as heating tube 13.

In FIG. 2, which shows a burner jet which is a regulating burner, tubular element 16 is formed as a heat exchanger from a refractory alloy with fins 21. This heat exchanger is constituted by sections of a certain length, for example 50 mm, which are assembled together. An outer tube shell 4 and a tube section 43 which is positioned in the axial extension of tube 4 coaxially surrounds tubular element or heat exchanger 16. At their facing extremities, tubes 4 and 43 are provided with respective flanges 24 and 25 which join the tubes together via a joint, which is not shown, and fix the burner to the wall of reactor 1, schematically shown at 44. The space delimited by tubes 4 and 43 is closed at the extremity opposite heating tube 13 by a tubular shell element 29 positioned in the axial extension of tube 43 and closed at its free extremity by a wall 30 which perpendicular to the axis of the tubular assembly. The facing extremities of tube 43 add shell element 29 are provided with connecting flanges 31, 32. Heat exchanger 16 is held at its extremity opposite abutment 18, which positions the heating tube, by radially extending elements 33 between flanges 31 and 32. Tube section is provided with an outlet 35 for evacuating burned gases from the reactor, while shell element 29 is provided with an inlet 36 to supply air for combustion. It can be seen that heat exchanger 16 separates the streams of air for combustion entering into the burner at 36 and the burned gases which circulate in a counter-current direction and exit the burner via outlet 35.

The fuel gas supply is ensured by a supply tube 37 which extends along the axis of rude 20 from wall 30 of shell element 29 into combustion chamber 14 through disk 15. The fuel gas(es) penetrate into chamber 14 via orifices 38, six for example, which are angularly distributed around the conduit forming a gas distributor near its extremity. The distributor 37 has a high voltage ignition means (39,40) at its extremity. An earth electrode shown at 39 is welded to the distributor while a high voltage electrode 40 is located on the distributor axis. This may be constituted by a rod of refractory alloy in an alumina sleeve. Air or oxidizer gas penetrates into combustion chamber 14 via holes P in heating tube 13, normally located in the same plane substantially perpendicular to the axis of the heating tube. Most often, the heating tube includes a number of planes for supply of air or oxidizer gas and the holes for air or oxidizer gas entry are formed so that the air or oxidizer gas penetrates into combustion chamber 14 along substantially tangential trajectories.

The burned gases leave combustion chamber 14 via exit 17 and penetrate directly into the inner tube which includes, in the embodiment shown in the figure, two sections 6a and 6b which form the inner shell of the blind tube forming heat exchange means 3. In this embodiment, heat exchange means 3 is a radiating recirculating blind tube which comprises an outer shell tube 4 which also forms the outer shell of the burner described above.

The tubes or shells of heat exchange means 3 are most often formed from a thermomechanical ceramic. However, it is within the scope of the present invention to use another material with suitable mechanical and chemical strength for the proposed use. In particular, outer shell 4 can be formed from a refractory alloy. The inner tube of heat exchange means 3 can be formed from a single section, but is more often composed of a number of sections, for example 2 to 12 sections, which are axially aligned and connected together by articulation means, i.e., flexible connecting means. It can be seen that tube sections 6a and 6b are positioned end-to-end. Each of the connecting means is formed as a sleeve 41, for example of ceramic, which coaxially surrounds the end-to-end extremities of the two connected tube sections 6a and 6b. The radially inner surface of sleeve 41 has, advantageously mid way along its length, an annular flange 42 which projects radially inwards and engages between the two extremities of the sections to be connected. The internal diameter of the flange substantially corresponds to the internal diameter of the tube sections 6a and 6b, while the external diameter of the flange is a little larger than the external diameter of the sections to allow a slight radial play to allow for slight misalignment of the sections while ensuring that the joint is sealed.

In one embodiment which is not shown in FIG. 2, the portions of the internal surface of sleeve 41 located either side of flange 42 have a diameter which gradually increases towards the extremity of the sleeves. The increase in the diameter is calculated so as to permit section 6a or 6b to follow any creep in shell tube 4 by an appropriate misaligning which can be of several degrees, in particular when this is formed of a refractory alloy. Shell tube 4 can thus be formed from a refractory alloy, i.e., a material with a coefficient of expansion and behavior at high temperature which is very different to the material constituting inner tube 6 (FIGS. 1A, 1B and 1C) (6a and 6b in FIG. 2).

Each sleeve 41 has centering ribs on its outer cylindrical surface (not shown in the Figures) for centering it in outer shell 4. The first and second tube sections 6 have centering ribs 45 at their free extremity and may include cut-outs or U shaped louvres formed in the cylindrical wall of the sections between the two centering ribs or vanes.

Inner tube 6 is open at both its extremities to allow the burned gases leaving the combustion chamber to circulate in the tube and in the annular space between inner tube 6 and shell tube 4, as shown by the arrows, the shell tube being closed at the extremity distant from the burner. The presence of louvres improves circulation of the combustion gases. Thus the radiant tube can be used in the vertical position even if the last section is bearing against the bottom of shell 4 following axial displacement of this section or a number of sections. For this reason, the axial half length of a sleeve is greater than the sum of the axial play between the tube, the adjacent elements and the different sections. Given that tube sections 6 have a constant internal and external diameter over their entire length, tube 6 can be simply cut to length to form sections or one section, or the tube can be constructed from a number of standard modules of different lengths.

It is often preferable to completely enclose the burner in one of the reactor walls as shown in FIG. 2. It is not beyond the scope of the invention, however, if this is not the case. Similarly, the position of the burner is generally selected so that the nozzle of the burner, i.e., exit 17 for the combustion gases, is located in immediate proximity to internal wall 44 of the reactor and preferably near this wall or slightly inside the zone between the two reactor walls.

The following examples illustrate the invention but do not limit its scope. They clearly demonstrate the flexibility of the apparatus of the present invention.

EXAMPLE 1

A horizontal reactor with a direct quenching facility was used with a total usable length of 7 m and a rectangular cross section of 1.5 m by 1.5 m. The configuration was similar to that shown in FIG. 1B.

The heat exchange means (3) comprised, as the heating means for the reactor, a burner whose burned gases supplied the inner shell (6) of a blind tube each forming a radiant heating element (3) of silicon carbide.

These heating elements were disposed in parallel layers perpendicular to the direction of circulation of the feed (vertical). Ceramic heating elements (3) had a length of 1.5 m and an external diameter of 165 mm; the distance ($E_g$) separating two neighbouring heating elements was 36 mm. The reactor included five longitudinal rows separated by a wall (11) of refractory electrosmelted alumina based concrete. The distance ($E_e$) between the heating elements (3) and the walls (11 or 12), or the passage width, was 18 mm. Each row consisted of 30 heating elements (3). Walls (11) and (12) were 99 mm thick at their thinnest part ($E_p$).

The first portion of each row, 1.4 m long, included 7 heating elements per row; in this portion, the feed introduced via input orifice (5), preheated to 1000° C., was heated to 1200° C. The temperature in this zone was regulated by thermocouples (7, FIG. 1A) located in the spaces where the feed circulated.

The second portion of each row, adjacent the first portion, was 4–6 m long: it was constituted by 23 heating elements (3) disposed in the same fashion as in the first portion of the row. Each heating element (3) comprised a regulation means to ensure that the temperature throughout this zone was 1200° C. plus or minus 10° C.

The effluent gases leaving the second portion were cooled to 800° C. by direct quenching in zone (8) which was 1 meter long and followed the second portion. Quenching was effected by introducing a C4 steam cracking cut via injectors (9).

The feed was constituted by methane containing 2% by weight of ethane diluted with hydrogen in a volume ratio (total hydrocarbons over hydrogen) of 1.1:1. This mixture was preheated to 1000° C. and cracked at 1200° C. in the reactor described above. The absolute pressure of the gas mixture at the reactor outlet was 0.140 MPa.

After cooling to room temperature, 22 kmoles of ethylene/acetylene mixture containing 70 mole % of acetylene was obtained from 500 kmoles of mixture.

EXAMPLE 2

The same reactor and a feed constituted by a butane/isobutane mixture containing 45 mole % of isobutane were used.

The first portion of each row, 2–8 m long, comprised 14 heating elements per row; in this row, the feed introduced via input orifice (5), preheated to 400° C., was heated to 900° C. The temperature in this zone was regulated by thermocouples (7, FIG. 1A) located in the spaces where the feed circulated.

The second portion of each row, adjacent the first portion, was 0.8 m long: it was constituted by 4 heating elements disposed in the same fashion as in the first portion of the row.

Such heating element (3) comprised a regulation means to heat the feed from 900° C. to 1000° C. and ensure that the temperature throughout this zone was maintained at 1000° C. plus or minus 10° C.

12 heat exchange means (3) remained available in each row. These heat exchange means (3) were used to indirectly quench the gases from 1000° C. to 840° C. To this end, the supply of fuel gas to the burner was cut off and the air flow was adjusted to effect the quench. The residual heat was recovered by direct exchange by introducing a C4 steam cracking cut via injectors (9).

The feed was constituted by a butane/isobutane mixture containing 45 moles of isobutane per 100 moles of mixture, diluted with nitrogen in a ratio of 1:3 by volume (total hydrocarbons over nitrogen). This mixture was preheated to 400° C. and cracked at 1000° C. in the reactor described above. The absolute pressure of the gas mixture at the reactor outlet was 0.140 MPa. After cooling to room temperature, 22 kmoles of ethylene/acetylene mixture containing 37 mole % of acetylene was obtained from 250 kmoles of mixture.

We claim:

1. An apparatus comprising:

a reactor elongated along one axis, having a reactor wall with an inner surface, a first end and a second end;

at least one supply means at said first end of said reactor for introducing at least one reactant, at least one discharge means at said second end of said reactor for removing effluents produced, a first zone within said reactor toward said first end of said reactor, said first zone having a plurality of heat exchange means arranged in substantially parallell layers perpendicular to said reactor axis to define open passages between said heat exchange means for circulation reactants, effluents or mixtures thereof, said heat exchange means are arranged in successive transverse sections that are independent and substantially perpendicular to said reactor axis, wherein at least some of said heat exchange means are tubular heat exchange elements each comprising at least one shell connected to a gas burner for supplying a combustion gas or combustion gas mixture as a heat exchange gas or gas mixture, and at least one outlet means for removing heat exchange gas or gas mixture, said gas burners are each connected to means for supplying fuel gas and oxidizer gas, and means for controlling said gas burners and adjusting the quantity of gas supplied to said gas burners, said means for controlling said gas burners are interposed between said means for supplying and said gas burners.

2. An apparatus according to claim 1, wherein said reactor further comprises a second zone toward said second end of said reactor, said second zone being contiguous with said first zone, and said second zone containing means cooling effluent connected to at least one means for supplying cooling fluid.

3. An apparatus according to claim 2, wherein said means for cooling effluent in said second zone is an indirect cooling means.

4. An apparatus according to claim 1, wherein said reactor further comprises means for controlling and adjusting heat exchange connected to said tubular heat exchange elements.

5. An apparatus according to claim 1, wherein each of said at least one shell has a longitudinal axis and said shell is elongated along said longitudinal axis.

6. An apparatus according to claim 1, wherein, in at least some of said tubular heat exchange elements, said at least one shell is an inner tube connected to said gas burner, said inner tube i.e. positioned within an outer shell forming an annular chamber around said inner tube, said annular chamber is in fluid communication with said inner tube, and said outlet means for removing heat exchange gas or gas mixture is also in fluid communication with said annular chamber.

7. An apparatus according to claim 1, wherein, in at least some of said tubular heat exchange elements, said at least one shell is an inner tubular shell positioned substantially coaxial within an outer tubular shell, whereby an annular free space is defined between said outer tubular shell and said inner tubular shell, said outer tubular shell is closed at one end, said inner tubular shell is open at both ends, said inner shell is connected at one open end thereof to said gas burner and said inner tubular shell at the other open end thereof is in fluid communication with said free space.

8. An apparatus according to claim 7, wherein said at least some tubular heat exchange elements each an additional shell which forms an annular chamber around said gas burner, and said outlet means is connected to said annular chamber for discharging heat exchange gas or gas mixture, wherein said annular chamber is in fluid communication with said annular free space, and wherein said outer tubular shell and said additional shell are coaxial and have the same internal diameter.

9. An apparatus according to claim 8, wherein said outer tubular shell and additional shell are formed by a single tube.

10. An apparatus according to claim 7, wherein said inner tubular shell has positioning ribs on its radially outer surface to position said inner tubular shell within said outer tubular shell.

11. An apparatus according to claim 7, wherein said inner tubular shell comprises a plurality of tube sections disposed end-to-end and substantially axially aligned, and adjacent tube sections are connected by an assembling means comprising an annular member forming a sleeve coaxially surrounding said adjacent tube sections to connect them together at a joint zone, the radially inner surface of said sleeve having at the mid-point of its length an annular flange which projects radially inwardly between the two adjacent tube sections to be connected, the portions of the inner surface situated either side of the flange widening gradually towards the extremities of the sleeve.

12. An apparatus according to claim 11, wherein the sleeve has radial centering ribs on outer surface for centering said inner tubular shell within said outer tubular shell.

13. An apparatus according to claim 1, wherein said some of said tubular heat exchange means form passive heat transfer elements.

14. An apparatus according to claim 1, wherein said reactor further comprises a second zone containing heat exchange means in which at least a portion of said heat exchange means in said second zone are connected to means for supplying at least one gas at a temperature lower than that of said combustion gas or combustion gas mixture.

15. An apparatus according to claim 14, wherein each of said heat exahange means in said second zone is connected to a burner and said at least one gas is oxidizer gas.

16. An apparatus according to claim 7, wherein the ratio of the inner area ($S_e$) of the cross section of said outer tubular shell to the outer area ($s_i$) of the cross section of said inner tubular shell is 1.4:1 to 25:1.

17. An apparatus according to claim 7, wherein the ratio of the inner area ($S_e$) of the cross section of said outer tubular shell to the outer area ($s_i$) of the cross section of said inner tubular shell is 2:1 to 9:1.

18. An apparatus according to claim 1, wherein said plurality of heat exchange means in said first zone are arranged in the form of an array in a triangular, square or rectangular pattern.

19. An apparatus according to claim 1, wherein said plurality of heat exchange means in said first zone are arranged in the form of at least two longitudinal zones, each zone comprising at least one row of heat exchange means and wherein said longitudinal zones are separated from each other by walls of refractory material.

20. An apparatus according to claim 19, wherein each of said walls of refractory material includes at least one means for equilibrating pressures in the longitudinal zone situated on either side of the refractory wall.

21. An apparatus according to claim 1, wherein said reactor further comprises projecting portions of ceramic material which extend inward from said inner surface of said reactor wall.

22. An apparatus according to claim 1, wherein the distance separating heat exchange means in said first zone is 2–100 mm.

23. An apparatus according to claim 19, wherein the distance between each of said heat exchange means and said walls is 1–100 mm.

24. An apparatus according to claim 23, wherein the distance between each of said heat exchange means and said walls is 2–50 mm.

25. An apparatus according to claim 19, wherein said walls, at their thinnest point, have a thickness of 2–300 mm.

26. An apparatus according to claim 19, wherein said walls, at their thinnest point, have a thickness of 5–50 mm.

* * * * *